(12) United States Patent
Malanchin et al.

(10) Patent No.: US 11,376,288 B2
(45) Date of Patent: Jul. 5, 2022

(54) METHODS OF USE OF PROBIOTIC COMPOSITIONS

(71) Applicant: ROELMI HPC S.R.L, Origgio (IT)

(72) Inventors: Rosella Malanchin, Origgio (IT);
Cristiana Piangiolino, Origgio (IT);
Marco Boccarusso, Origgio (IT)

(73) Assignee: SYNBALANCE SRL, Origgio (IT)

( * ) Notice: Subject to any disclaimer, the term of this patent is extended or adjusted under 35 U.S.C. 154(b) by 0 days.

(21) Appl. No.: 16/949,312

(22) Filed: Oct. 26, 2020

(65) Prior Publication Data
US 2021/0046129 A1 Feb. 18, 2021

Related U.S. Application Data

(63) Continuation of application No. 16/064,376, filed as application No. PCT/EP2016/082190 on Dec. 21, 2016, now abandoned.

(30) Foreign Application Priority Data

Dec. 22, 2015 (IT) .......................... 102015000086645

(51) Int. Cl.
| | |
|---|---|
| *A61K 35/745* | (2015.01) |
| *A61K 35/747* | (2015.01) |
| *A61K 35/741* | (2015.01) |
| *A61P 15/00* | (2006.01) |

(52) U.S. Cl.
CPC .......... *A61K 35/745* (2013.01); *A61K 35/741* (2013.01); *A61K 35/747* (2013.01); *A61P 15/00* (2018.01)

(58) Field of Classification Search
None
See application file for complete search history.

(56) References Cited

U.S. PATENT DOCUMENTS

| | | | |
|---|---|---|---|
| 8,309,075 B2 | 11/2012 | Albers et al. | |
| 9,233,130 B2 | 1/2016 | Mogna et al. | |
| 9,492,377 B2* | 11/2016 | Mogna | .................. A61K 9/205 |
| 2011/0027243 A1 | 2/2011 | Mogna et al. | |
| 2014/0234259 A1 | 8/2014 | Juras | |
| 2017/0014335 A1 | 1/2017 | Mogna et al. | |

FOREIGN PATENT DOCUMENTS

| | | |
|---|---|---|
| KR | 2014037544 A | 3/2014 |
| WO | 2009/071578 A1 | 6/2009 |
| WO | 2012/101500 A1 | 8/2012 |
| WO | 2014/093486 A1 | 6/2014 |

OTHER PUBLICATIONS

Presti et al. "Evaluation of the probiotic properties of new *Lactobacillus* and *Bifidobacterium* strains and their in vitro effect". Appl Microbiol Biotechnol., Mar. 2015, 99, pp. 5613-5626.*
D'Orazio et al. "Microencapsulation of new probiotic formulations for gastrointestinal delivery: in vitro study to assess viability and biological properties". Appl Microbiol Biotechnol., Aug. 2015, 99, pp. 9779-9789.*
Hoesl et al., "The Probiotic Approach: An Alternative Treatment Option in Urology", European Urology, 2005, pp. 288-296, vol. 47, No. 3.
Zuccotti et al., "Probiotics in clinical practice: An overview", The Journal of International Medical Research, 2008, pp. 1A-53A, vol. 36, No. Suppl. 1.
International Search Report and Written Opinion, dated Apr. 5, 2017, from corresponding PCT application No. PCT/EP2016/082190.
International Preliminary Report, dated Dec. 21, 2017, from corresponding PCT application No. PCT/EP2016/082190.
D'Orazio et al. "Microencapsulation of new probiotic formulations for gastrointestinal delivery: in vitro study to assess viability and biological properties". Appl Microbiol Biotechnol. 2015, 99, pp. 9779-9789; published online Aug. 5, 2015.
Presti et al. "Evaluation of the probiotic properties of new *Lactobacillus* and *Bifidobacterium* strains and their in vitro effect". Appl Microbiol Biotechnol. 2015, 99, pp. 5613-5626; published online Mar. 7, 2015.

* cited by examiner

*Primary Examiner* — Vera Afremova

(74) *Attorney, Agent, or Firm* — Nixon & Vanderhye

(57) ABSTRACT

Disclosed are methods of using probiotic compositions containing *Lactobacillus plantarum*, *Lactobacillus rhamnosus*, and *Bifidobacterium animalis* subsp. *lactis*. to prevent and/or treat urogenital infections in women by oral administration.

16 Claims, 5 Drawing Sheets

METHODS OF USE OF PROBIOTIC COMPOSITIONS

CROSS-REFERENCE TO RELATED APPLICATION

This application is a divisional of U.S. Ser. No. 16/064,376 filed Jun. 20, 2018, which was a national stage application, filed under 35 U.S.C. § 371, of International Patent Application No. PCT/EP2016/082190 filed 2016 Dec. 21, which claims priority to IT application No. 102015000086645 filed 2015 Dec. 22. Each of the previously noted applications is hereby incorporated by reference in their entirety.

FIELD OF THE INVENTION

The present invention relates to probiotic compositions containing *Lactobacillus plantarum*, *Lactobacillus rhamnosus*, *Bfidobacterium animalis* subsp. *lactis*. Such compositions are useful to prevent and/or treat urogenital infections in women by oral administration.

BACKGROUND OF THE INVENTION

A large number of symbiont microorganisms colonize the human body, which all together form the human microbiota. The vaginal microbiota is composed of species which are present in the vaginal mucosa and may vary significantly in pre- and postmenopausal women. The microbiota of healthy premenopausal women is generally composed of lactobacilli, such as for example, the Döderlein's lactobacilli, mainly belonging to the *Lactobacillus acidophilus* spp., but also to other species of *Lactobacillus*: for example *L. fermentum*, *L. vaginalis*, *L. plantarum*, *L. delbrueckii*, *L. brevis*, *L. reuteri*, *L. casei*, *L. rhamnosus*.

The vaginal microbiota is affected by hormonal changes (mainly by estrogen levels in pregnancy or in menopause), by drugs consumption, by vaginal pH (affected by antibiotics), etc.

Urogenital infections may be:

Bacterial vaginosis, mainly associated to *Gardnerella vaginalis*, to *Atopobium vaginae*, to *Bacteroides* (such as *Prevotella*) and to other pathogenic agents. It affects women of all ages, it is often asymptomatic and it is characterized by a high vaginal pH value (>4.5) and by *Lactobacillus* depletion.

Fungal vaginitis, mainly caused by *Candida albicans* (candidiasis) but also by other species of *Candida* or by *Trichomonas vaginalis*, is characterized by white secretions, local pruritis and irritation.

Cystitis, mainly caused by *Escherichia coli* and *Enterococcus faecalis*, occurs when pathogenic bacteria present in the bowel get into the urethra through the anus and start to replicate within the bladder. Acute cystitis causes frequent painful urinations and in many cases becomes recurrent.

These three examples of urogenital infections are characterized by acute inflammatory conditions that may result in chronic cases.

Globally, more than 1 billion of urogenital infection cases are reported every year, 27-48% of these are recurrent. Standard therapies require the use of specific antibiotics or antifungal, orally or locally administrated. However, these treatments weaken the immune system of the vaginal area, they are not indicated for frequent or recurrent therapies and, above all, they are less effective due to the spreading of drug-resistant bacteria.

In light of the above, there is still the need to identify effective alternative solutions in order to prevent and/or treat urogenital infections in women, also in recurrent cases.

SUMMARY OF THE INVENTION

The present invention relates to probiotic compositions containing *Lactobacillus plantarum*, *Lactobacillus rhamnosus*, *Bifidobacterium animalis* subsp. *lactis*.

Moreover, the invention relates to the use of such compositions in the prevention and/or treatment of female urogenital infections and their relapses.

DETAILED DESCRIPTION OF THE INVENTION

Figure 1:
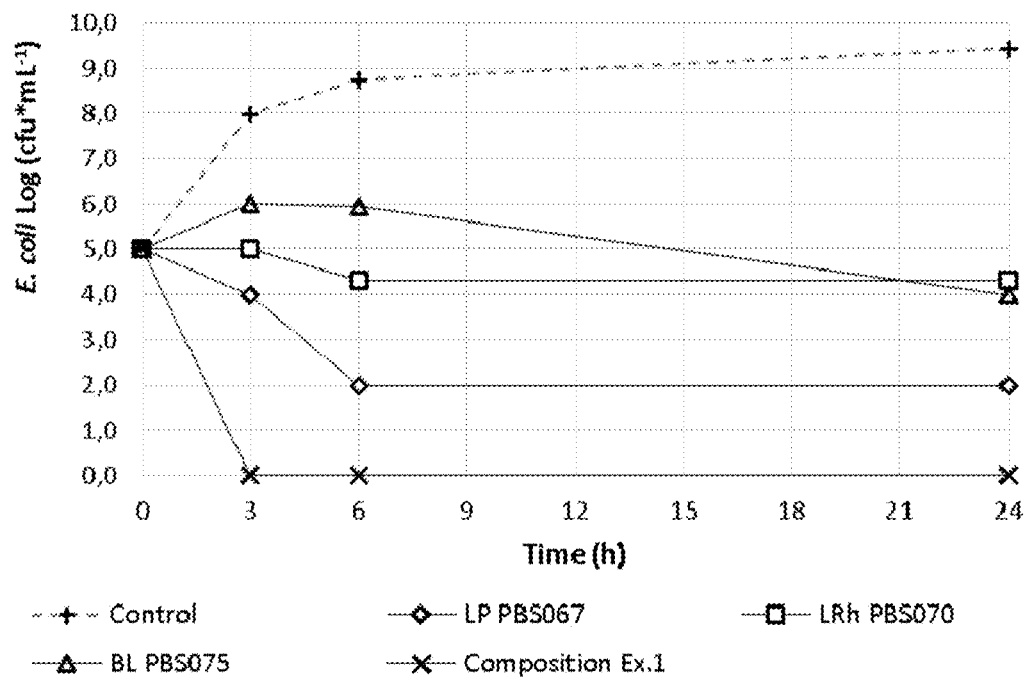
FIG. 1 shows the antimicrobial activity against *Escherichia coli* (ATCC 25922) in the cell-free supernatants mediated by metabolites secreted from the probiotic composition of Example 1 compared to single strains, assessed by broth microdilution method.

The present invention relates to compositions containing three different probiotic species: *Lactobacillus plantarum*, *Lactobacillus rhamnosus* and *Bifidobacterium animalis* subsp. *lactis*.

Surprisingly, it was found that compositions containing *Lactobacillus plantarum*, *Lactobacillus rhamnosus* and *Bifidobacterium animalis* subsp. *lactis* show a synergistic effect to prevent and/or to treat female urogenital infections.

The probiotic composition of the invention does not comprise a prebiotic component comprising at least one scFOS, short-chain fructo-oligosaccharide.

According to a preferred aspect of the invention, the compositions contain a preferred strain of each of the three different probiotic species, in particular the compositions may contain *Lactobacillus plantarum* PBS067, *Lactobacillus rhamnosus* PBS070 and *Bifidobacterium animalis* subsp. *lactis* PBS075.

*Lactobacillus plantarum* strain called "PBS067" was deposited in the Leibniz-Institut DSMZ-Deutsche Sammlung von Mikroorganismen und Zellkulturen GmbH, under the Budapest Treaty, on Jun. 6, 2011, obtaining Accession Number "DSM 24937".

*Lactobacillus rhamnosus* strain called "PBS070" or "LRH020" was deposited in the Leibniz-Institut DSMZ-Deutsche Sammlung von Mikroorganismen und Zellkulturen GmbH, under the Budapest Treaty, on Jan. 17, 2012, obtaining Accession Number "DSM 25568".

*Bifidobacterium animalis* subsp. *lactis* strain called "PBS075" or "BL050" has been deposited in the Leibniz-Institut DSMZ-Deutsche Sammlung von Mikroorganismen und Zellkulturen GmbH, under the Budapest Treaty, on Jan. 17, 2012, obtaining Accession Number "DSM 25566".

The present invention relates to compositions containing *Lactobacillus plantarum*, *Lactobacillus rhamnosus* and *Bifidobacterium animalis* subsp. *lactis*, preferably *Lactobacillus plantarum* PBS067, *Lactobacillus rhamnosus* PBS070 and *Bifidobacterium animalis* subsp. *lactis* PBS075, in a mixture with at least one physiologically acceptable excipient or carrier; preferred compositions are not micro-encapsulated.

Compositions may be formulated through conventional methods. Preferred forms of administration are solid formulations, such as hard capsules, sachets, tablets, powder, softgels, or liquid formulations, such as drops, douches, vials.

*Lactobacillus plantarum* (LP), preferably strain *Lactobacillus plantarum* PBS067, can be present in the composition in different quantities on the composition's total weight from 10 mg to 90 mg, preferably from 25 mg to 50 mg, even more preferably 33 mg.

*Lactobacillus rhamnosus* (LRh), preferably strain *Lactobacillus rhamnosus* PBS070, can be present in the composition in different quantities on the composition's total weight from 10 mg to 90 mg, preferably from 25 mg to 50 mg, even more preferably 33 mg.

*Bifidobacterium animalis* subsp. *lactis* (BL), preferably strain *Bifidobacterium animalis* subsp. *lactis* PBS075, can be present in the composition in different quantities on the composition's total weight from 10 mg to 90 mg, preferably from 25 mg to 50 mg, even more preferably 33 mg.

The three species of *Lactobacillus plantarum*, *Lactobacillus rhamnosus* and *Bifidobacterium animalis* subsp. *lactis* can be present in a weight ratio of 1:1:1, preferably in a composition of 100 mg in which each strain is present at a concentration of 100 B CFU/g each.

Preferably the probiotic compositions of the invention is administered orally.

An additional object of the present invention is the use of the probiotic compositions comprising *Lactobacillus plantarum*, *Lactobacillus rhamnosus* and *Bifidobacterium animalis* subsp. *lactis*, preferably *Lactobacillus plantarum* PBS067, *Lactobacillus rhamnosus* PBS070 and *Bifidobacterium animalis* subsp. *lactis* PBS075, to prevent and/or to treat urogenital infections in women and their relapses.

According to a preferred aspect of the invention, the female urogenital infections prevented and/or treated with the probiotic compositions of the invention, may be bacterial vaginosis, for example associated to *Gardnerella vaginalis*, or to *Atopobium vaginae*, or to *Bacteroides* (such as *Prevotella*) or to other pathogens; fungal vaginosis, or candidiasis, mainly caused by *Candida* or by *Trichomonas vaginalis*; cystitis, mainly caused by *Escherichia coli*.

The following examples further illustrate the invention.

EXAMPLES

Example 1 of Formulation

The composition in powder form contains:

| POWDER COMPOSITION | | Unit |
| --- | --- | --- |
| LP 500B (equivalent to 10 mg of LP 300B) | 6.0 | mg |
| LRh 300B | 10.0 | mg |
| BL 300B | 10.0 | mg |

Example 2 of Formulation

The composition in powder form in capsules contains:

| COMPOSITION PER CAPSULE | | Unit |
| --- | --- | --- |
| LP 500B | 12.0 | mg |
| LRh 300B | 20.0 | mg |
| BL 300B | 60.0 | mg |
| Inulin | 298.0 | mg |
| Silicon dioxide | 5.0 | mg |
| Talc | 5.0 | mg |
| Total | 400.0 | mg |

Example 3 of Formulation

The composition in powder form in capsules contains:

| COMPOSITION PER CAPSULE | | Unit |
| --- | --- | --- |
| LP 500B | 20.0 | mg |
| LRh 300B | 33.0 | mg |

-continued

| COMPOSITION PER CAPSULE | | Unit |
|---|---|---|
| BL 300B | 33.0 | mg |
| Magnesium stearate | 4.5 | mg |
| Silicon dioxide | 4.5 | mg |
| Cornstarch | 260.0 | mg |
| Total | 355.00 | mg |

Example 4 of Formulation

The composition in powder form in sachets contains:

| COMPOSITION PER SACHET | | Unit |
|---|---|---|
| LP 500B | 40.0 | mg |
| LRh 300B | 66.0 | mg |
| BL 300B | 16.7 | mg |
| Vitamin B6 | 298.00 | mg |
| Vitamin B9 | 5.00 | mg |
| Vitamin B12 | 5.00 | mg |
| Silicon dioxide | 20.0 | mg |
| Maltodextrin | 1349.3 | mg |
| Cornstarch | 200.0 | mg |
| Total | 2000.00 | mg |

Example 5 of Formulation

The composition in powder form in sachets contains:

| COMPOSITION PER SACHET | | Unit |
|---|---|---|
| LP 500B | 10.0 | mg |
| LRh 300B | 16.5 | mg |
| BL 300B | 16.5 | mg |
| Vitamin B3 | 22.4 | mg |
| Zinc oxide | 12.5 | mg |
| Silicon dioxide | 20.0 | mg |
| Maltodextrin | 1702.1 | mg |
| Cornstarch | 200.0 | mg |
| Total | 2000.00 | mg |

The following experimental examples show the antimicrobial activity of the composition of the invention against urogenital pathogens and the enhanced anti-inflammatory activity and the antioxidant power of the probiotic composition of Example 1 compared to the single strains administered individually.

Antimicrobial Activity

The antimicrobial activities of fermentation metabolites secreted from the probiotic composition of the invention were investigated and quantified by measuring the growth inhibition of *Escherichia coli* ATCC 25922 and *Candida albicans* ATCC 10231 in liquid cultures in the presence of 25% (v/v) Cell-Free culture Supernatants by the broth microdilution method.

Direct inhibition of *Escherichia coli* ATCC 25922 and *Candida albicans* ATCC 10231 was assayed by the overlay method, as described by Presti et al., 2015, page 4, par. Antimicrobial activity of lactobacilli and bifidobacteria strains by using living cells. This in vitro assay provides a representative situation for the competition among probiotic and pathogenic bacteria as happens in vivo for the colonization of the vaginal epithelium.

Example 6—Anti *E. coli* Activity of Broth Fermentation Metabolites

Table 1 reports the results of the growth inhibition of *E. coli* by broth microdilution method over 24 hours, in presence of 25% (v/v) of Cell-Free Supernatant. Single strains were effective if compared to control without CFS, but the metabolites in CFS from the probiotic composition of Example 1 gained a total *E. coli* inhibition within 3 hours. The results are shown also in FIG. 1.

TABLE 1

| Cell-Free | *Escherichia coli* Log (CFU/ml) | | | |
|---|---|---|---|---|
| Supernatant | T0 | T3 | T6 | T24 |
| None | 5.0 | 8.0 | 8.7 | 9.4 |
| LP PBS067 | 5.0 | 4.0 | 2.0 | 2.0 |
| LRh PBS070 | 5.0 | 5.0 | 4.3 | 4.3 |
| BL PBS075 | 5.0 | 6.0 | 6.0 | 4.0 |
| Composition Ex. 1 | 5.0 | <1.0 | <1.0 | <1.0 |

Figure 2:
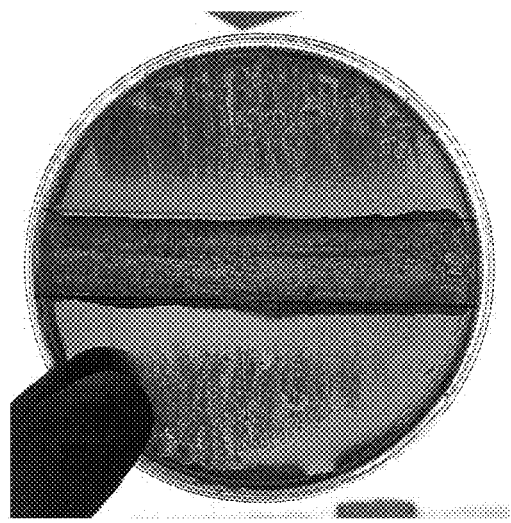
FIG. 2 shows the antimicrobial activity of the probiotic composition of Example 1 against *Escherichia coli* (ATCC 25922), assessed by agar overlay method.
Figure 3:
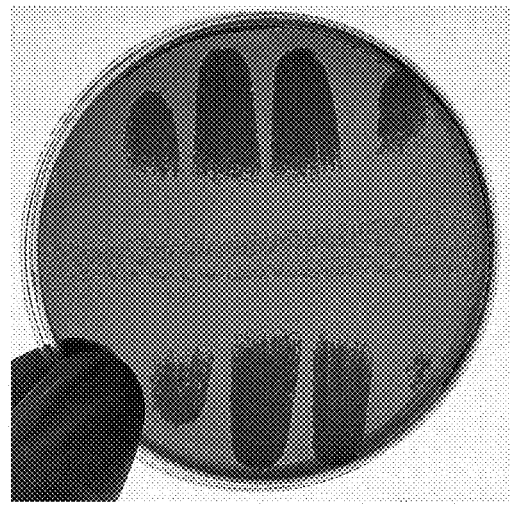
FIG. 3 shows the antimicrobial activity of the probiotic composition of Example 1 against *Candida albicans* (ATCC 10231), assessed by agar overlay method.

Example 7 and Example 8—Direct Inhibition of *E. coli* and *C. albicans* Respectively Table 2 reports the millimeters of the inhibition halo measured by the modified agar overlay method against *E. coli* and *C. albicans*, as shown in FIG. 2 and in FIG. 3 respectively. Pathogens were seeded over all the overlaid agar surface, but they couldn't growth near the probiotic, seeded only on a horizontal stripe. The size of the inhibition halo is indicative of the antimicrobial strength: a bigger halo correspond to a stronger antimicrobial activity.

TABLE 2

| Sample | *Escherichia coli* | *Candida albicans* |
|---|---|---|
| | Inhibition halo (mm) | |
| LP PBS067 | 8 | 5 |
| LRh PBS070 | 7 | 8 |
| BL PBS075 | 6 | 1 |
| Composition Ex. 1 | 11 | 15 |

As clearly shown in Examples 6, 7, 8 specific antimicrobial activities against urogenital pathogens, *Escherichia coli* ATCC 25922 and *Candida albicans* ATCC 10231, the composition of the invention combining the three strains allow to achieve an increase of the antimicrobial activity compared to the activity shown individually by each strain.

Thus, the effect obtainable by administering the composition according to the invention is higher than the sum of the individual effects obtainable by administering the single strains separately (considering that the total amount of the composition of the invention used in tests is equal to the total amount of each strain individually administered, so the amount of each strain in the tested composition of the invention is equal to ⅓ of the amount of each individually tested strain).

In other words, the interaction of the individual strains produces an evident synergistic effect against urogenital pathogens.

In other words, the interaction between the individual strains in the composition of the invention leads to a clear synergistic effect.

Anti-Inflammatory Activity and Antioxidant Power

Bacterial urogenital infections are widespread inflammatory diseases. Cytokines in the host play an essential role in both the initial and the long-term immune response and inflammation process.

Inflammation is not only as a consequence of pathogen infections, but in turn it can also be a cause of such infections.

An homeostasis imbalance between inflammation and immune system leads to a less effective immune response, opening the way to pathogenic infections.

The first mechanism of protection in the host is the innate immunity. Innate immune cells express genetically encoded receptors, called Toll-like receptors (TLRs). Human genitourinary cells respond to microbial surface molecules with Toll-like receptors-2, 4 and 6, which trigger the transcription of pro-inflammatory cytokines such as IL-1a, IL-1b, IL-6 and TNF-α.

On the other hand, adaptive immune response is linked to lymphocyte activation regulated by cytokines. This causes the B cells or T cells to proliferate and differentiate into specialized effector lymphocytes. The interleukin 4 (IL-4) is a cytokine that induces differentiation of naive helper T cells (Th0 cells to Th2 cells). IL-4 is the positive feedback cytokine for Th2 cells differentiation. Besides, IL-4 stimulates B-cells to produce antibodies.

TNF-α and IL-4 have been selected as representative biomarkers for pro-inflammatory and anti-inflammatory cytokines, respectively, to demonstrate the efficacy of probiotics in modulating the inflammatory status.

The mixture of freeze-dried probiotic strains (LP PBS067, LRh PBS070 and BL PBS075) has been prepared as described in Example 1, for a total of 100 mg ($3*10^9$ $cfu*g^{-1}$). The mixture has been suspended in 100 ml of DMEM (Dulbecco's Modified Eagle's Medium) at a concentration of $10^8$ $cfu*ml^{-1}$ and preserved at 4° C. until its use.

An in vitro experimental study on fibroblasts Balb 3T3 CLONE 31 (ATCC-CCL-163) was carried out. Fibroblasts Balb 3T3 CLONE 31 represent a systemic cell line used for medical device's safety tests and they are also predictive for the vaginal mucosa.

The inflammation has been induced by adding 0.01% of SDS (sodium dodecyl sulfate).

Cells has been treated with 1 ml of mixture at total concentration of $10^7$ $cfu*ml^{-1}$ and with 1 ml of each strain, each with a concentration of $10^7$ $cfu*ml^{-1}$.

The positive control CTR+ is made up of cells that have been treated only with SDS, while the negative control is represented by untreated cells.

The effect on the production and inhibition of cytokines was evaluated, in particular on the inhibition of TNF-α and on the production of interleukin 4 (IL-4) by the cellular system and its change in terms of embedded antioxidant power after 24 h (acute inflammation) and after 5 days (chronic inflammation).

Cytokines' dosages have been measured by means of kit ELISA while the antioxidant power has been evaluated through the FRAP test.

Figure 4:
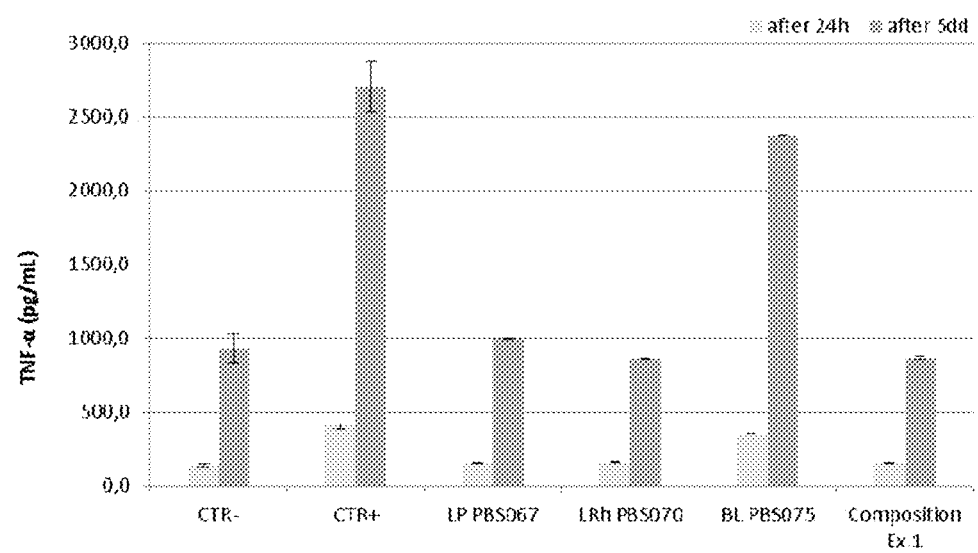
FIG. 4 shows the quantification of the pro-inflammatory cytokine TNF-α determined by ELISA to assess the anti-inflammatory activity mediated by the probiotic composition of Example 1 and by the single strains, compared to negative and positive controls. Inflammatory stress on fibroblast cell line BALB/3T3, clone A31, was induced by Sodium Dodecyl Sulfate in positive control and test samples. The evaluation was carried out after 24 h and 5 days from each treatment.

Example 9—Evaluation of the Effects on TNF-α Inhibition, Pro-Inflammatory Cytokine (Pro-I) with Early Release Table 3 reports the results of TNF-α inhibition obtained by single strains LP PBS067, LRh PBS070 and BL PBS075 and by the mixture of the three strains LP PBS067, LRh PBS070 and BL PBS075 (probiotic composition of Example 1), compared to negative and positive controls. The results are shown also in FIG. 4.

TABLE 3

| STRAIN | TNF-α (pg/mL) | | | |
|---|---|---|---|---|
| | after 24 h | after 5dd | SD 24 h | SD 5gg |
| CTR− | 139.70 | 932.27 | 11.82 | 101.75 |
| CTR+ | 406.23 | 2706.90 | 21.40 | 172.79 |
| LP PBS067 | 151.03 | 992.87 | 3.11 | 8.48 |
| LRh PBS070 | 158.37 | 857.10 | 56.24 | 48.04 |
| BL PBS075 | 355.07 | 2375.20 | 11.66 | 45.28 |
| Composition of Example 1 | 151.70 | 867.00 | 10.00 | 67.90 |

Figure 5:
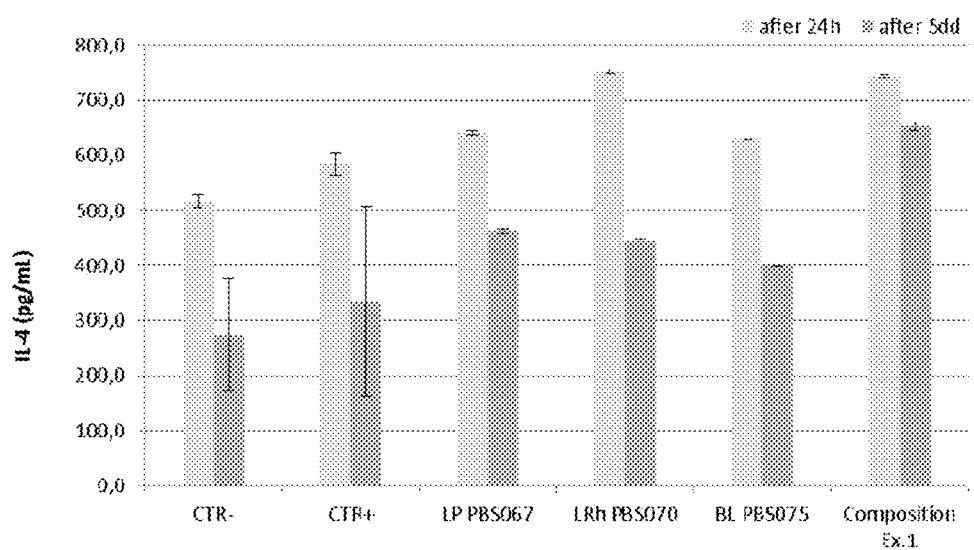
FIG. 5 shows the quantification of the anti-inflammatory cytokine IL-4 determined by ELISA to assess the anti-inflammatory activity of the probiotic composition of Example 1 and by the single strains, compared to negative and positive controls. Inflammatory stress on fibroblast cell line BALB/3T3, clone A31, was induced by Sodium Dodecyl Sulfate in positive control and test samples. The evaluation was carried out after 24 h and 5 days from each treatment.

Example 10—Evaluation of the Effects on the Production of IL-4, an Anti-Inflammatory Cytokine (Anti-I) with Late Release Table 4 reports the results of IL-4 secretion obtained by single strains LP PBS067, LRh PBS070 and BL PBS075 and by the mixture of the three strains LP PBS067, LRh PBS070 and BL PBS075 (probiotic composition of Example 1), compared to negative and positive controls. The results are shown also in FIG. 5.

TABLE 4

| STRAIN | IL-4 (pg/mL) | | | |
|---|---|---|---|---|
| | after 24 h | after 5dd | SD 24 h | SD 5gg |
| CTR− | 516.53 | 273.93 | 4.82 | 34.87 |
| CTR+ | 584.20 | 335.03 | 13.40 | 45.60 |
| LP PBS067 | 641.83 | 461.53 | 16.07 | 60.82 |
| LRh PBS070 | 752.57 | 444.67 | 19.45 | 24.59 |
| BL PBS075 | 628.13 | 398.80 | 5.00 | 19.40 |
| Composition of Example 1 | 744.30 | 654.50 | 5.70 | 6.83 |

Example 11—Evaluation of the Effects on Cellular Antioxidant Power

Figure 6:
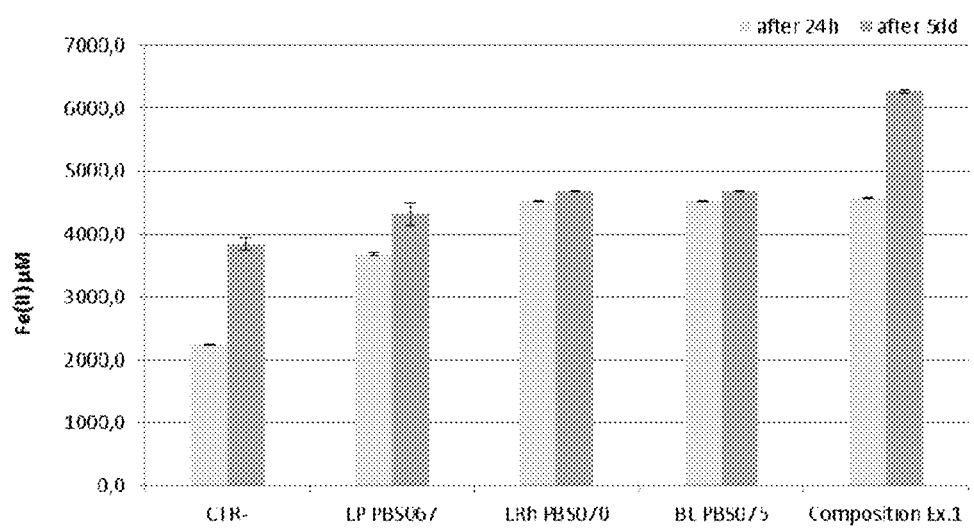
FIG. 6 shows the antioxidant power determined as Ferric Reducing Antioxidant Parameter (FRAP) of the probiotic composition of Example 1 and of the single strains, compared to negative control, on fibroblast cell line BALB/3T3, clone A31. The evaluation was carried out on fibroblast cell line BALB/3T3, after 24 h and 5 days from treatments.

Table 5 reports the results on the antioxidant power assayed by FRAP test of single strains LP PBS067, LRh PBS070 and BL PBS075 and of the mixture of the three strains LP PBS067, LRh PBS070 and BL PBS075 (probiotic composition of example 1) compared to negative control. The results are shown also in FIG. 6.

TABLE 5

| STRAIN | FRAP - Fe(II) μM | | | |
|---|---|---|---|---|
| | after 24 h | after 5dd | SD 24 h | SD 5gg |
| CTR− | 2238.78 | 3842.30 | 160.24 | 346.19 |
| LP PBS067 | 3678.03 | 4321.23 | 1051.52 | 41.91 |
| LRh PBS070 | 4519.40 | 4684.50 | 1517.88 | 39.81 |
| BL PBS075 | 2881.80 | 4198.53 | 116.44 | 312.676 |
| Composition of Example 1 | 4565.00 | 6273.30 | 163.90 | 104.10 |

The following experimental examples provide the evaluation of the predictive efficacy of the composition of the Example 2 on vaginal pH, on the symptoms of the infection and on the colonization of the vaginal epithelium by the strain orally administered assessed in a peer-reviewed study.

This study consisted of a randomized, double blinded and placebo controlled pilot study. It involved forty pre-menopausal women aged between 18 and 50 years old. The forty volunteers were divided into two groups of treatment on a random basis; each group was treated, for 14 days, with the formulation of Example 2 or with placebo, respectively. The enrolled subjects had a gynecological examination and vaginal swabs were collected in order to take a sample of vaginal secretion, at four experimental times: the day before first intake of formulation/placebo, after 7, 14 and 21 days from the first intake (day 21 represents seven days after the end of the treatment). Quantification of the probiotic strains was carried out by qPCR analysis on total DNA extract from vaginal swabs. Furthermore, a self-assessment questionnaire was administered at T0 and at T21 to assess the effects of the treatment.

Example 12—Evaluation of the Effects on Vaginal pH

Figure 7:
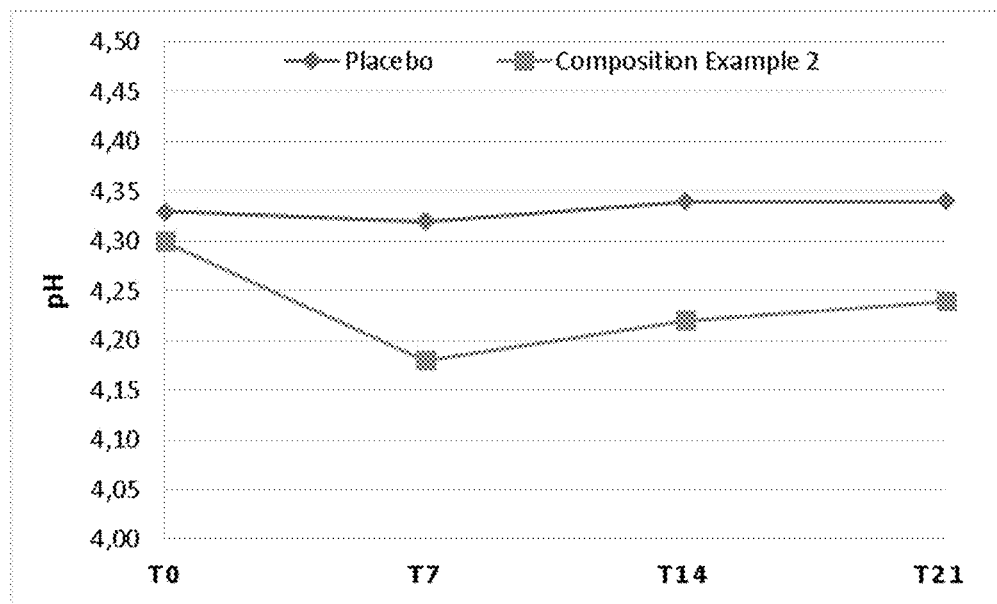
FIG. 7 shows the effects of the composition of the invention compared to placebo on vaginal pH measured in a randomized, double blinded, placebo controlled pilot study during 14 days of treatment with the probiotic composition of Example 2 or with placebo. Day 21 represents seven days after the end of the treatment.

During the treatment with formulation of Example 2 a variation of vaginal pH compared to the placebo was observed, starting from the same baseline values at T0. This trend is due to the colonization by probiotic strains which produce organic acids that are responsible for the acidification of the vaginal environment. Results are shown in FIG. 7.

Example 13—Evaluation of the Effects on Symptoms

Figure 8:
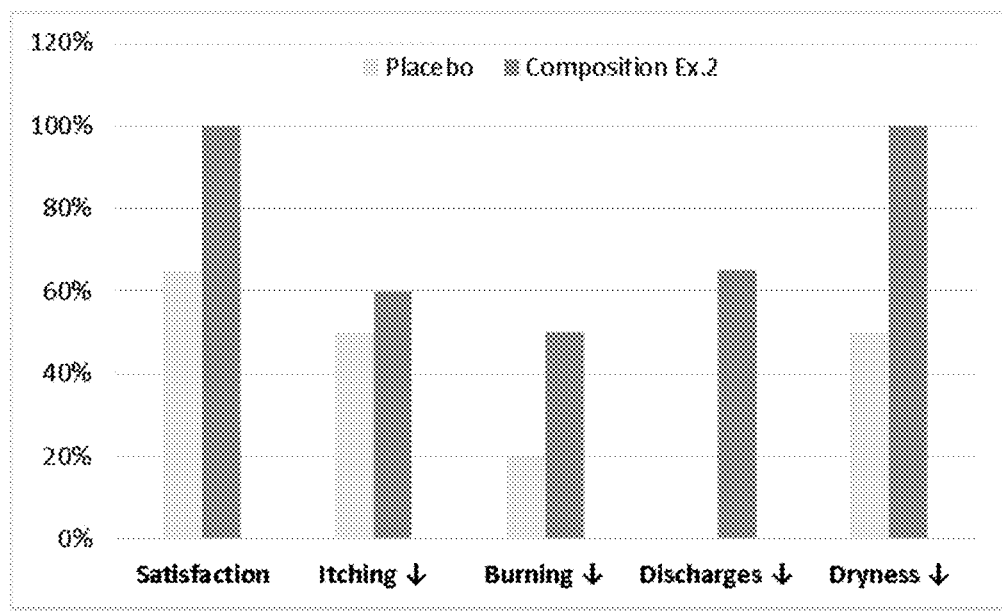
FIG. 8 shows the mean results obtained through a self-assessment questionnaire related to subjective perception for considered symptoms: itching decrease, decreasing of burning sensation, decreasing discharges, dryness decrease; in a randomized, double blinded, placebo controlled pilot study of women treated with the probiotic composition of Example 2 compared to the placebo group.

The subjective perception of the women involved in the treatment was evaluated using a self-assessment questionnaire: an almost total satisfaction was observed in the group treated with the composition of the invention compared to placebo. An improvement in the normal symptoms, not associated with disease, such as itching, burning sensations, vaginal discharge and dryness was detected. Results are shown in FIG. 8.

Figure 9:
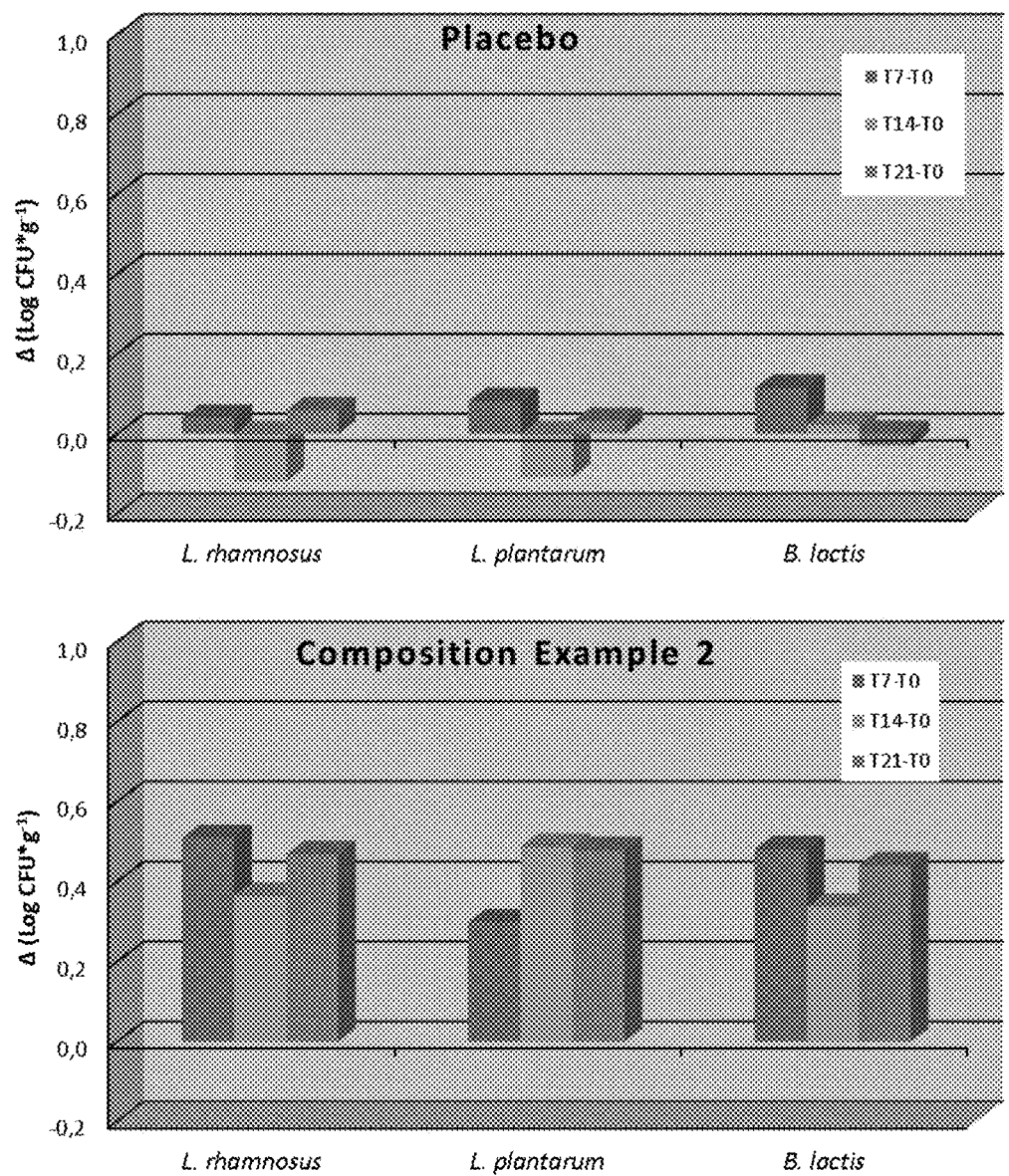
FIG. 9 shows the results related to the ability of the strains of the probiotic composition of Example 2 compared to placebo to colonize the Vaginal Epithelium Cells (VEC) in a randomized, double blinded, placebo controlled pilot study. The quantification of probiotic strains was made by qPCR analysis on total DNA extract from vaginal swabs collected at TO, T7, T14, T21 days. Charts report the delta between the quantification during treatment (T7, T14 and T21) and the quantification before treatment (TO).

Example 14—Evaluation of the Effectiveness of Probiotics in Vaginal Colonization The effectiveness of the strains of the composition of the invention in colonizing the vaginal epithelium is provided by means of a real-time quantitative PCR technique upon vaginal swabs. This instrumental test identified the increase of the administered strains only and quantified their presence in comparison to placebo. Results are shown in FIG. 9.

The invention claimed is:

1. A method for the prevention and/or treatment of female urogenital infections and relapses thereof comprising administering to a subject in need thereof an effective amount of a probiotic composition comprising:
   Lactobacillus plantarum PBS067 accession number DSM24937,
   Lactobacillus rhamnosus LRH020 accession number DSM25568, and
   Bifidobacterium animalis subsp. lactis BL050 accession number DSM 25566,
   and preventing and/or treating female urogenital infections and relapses thereof in said subject, provided that the probiotic composition does not comprise a prebiotic component comprising at least one short-chain fructo-oligosaccharide ($_{sc}$FOS).

2. The method of claim 1, wherein the composition is a solid formulation in form of hard capsules, sachets, tablets, powder or soft-gels, or a liquid formulation in form of drops, douches or vials.

3. The method of claim 1, wherein Lactobacillus plantarum is present in amounts on the total weight of the composition ranging from 10 mg to 90 mg.

4. The method of claim 1, wherein Lactobacillus rhamnosus is present in amounts on the total weight of the composition ranging from 10 mg to 90 mg.

5. The method of claim 1, wherein Bifidobacterium animalis subsp. lactis is present in amounts on the total weight of the composition ranging from 10 mg to 90 mg.

6. The method of claim 1, wherein Lactobacillus plantarum:Lactobacillus rhamnosus:Bifidobacterium animalis subsp. lactis are present in a ratio of 1:1:1.

7. The method of claim 1, wherein the composition is administered orally.

8. The method of claim 1, wherein the female urogenital infection is bacterial vaginosis.

9. The method of claim 1, wherein the female urogenital infection is fungal vaginitis.

10. The method of claim 1, wherein the female urogenital infection is cystitis.

11. The method of claim 1, wherein Lactobacillus plantarum is present in amounts on the total weight of the composition ranging from 25 mg to 50 mg.

12. The method of claim 1, wherein Lactobacillus rhamnosus is present in amounts on the total weight of the composition ranging from 25 mg to 50 mg.

13. The method of claim 1, wherein Bifidobacterium animalis subsp. lactis is present in amounts on the total weight of the composition ranging from 25 mg to 50 mg.

14. The method of claim 1, wherein Lactobacillus plantarum is present in an amount on the total weight of the composition of 33 mg.

15. The method of claim 1, wherein Lactobacillus rhamnosus is present in an amount on the total weight of the composition of 33 mg.

16. The method of claim 1, wherein Bifidobacterium animalis subsp. lactis is present in an amount on the total weight of the composition of 33 mg.

* * * * *